United States Patent [19]
Feng

[11] Patent Number: 5,421,343
[45] Date of Patent: Jun. 6, 1995

[54] COMPUTER NETWORK EEMPI SYSTEM

[76] Inventor: Genquan Feng, P.O. Box 1796, New York, N.Y. 10185-0016

[21] Appl. No.: 63,460

[22] Filed: May 17, 1993

Related U.S. Application Data

[63] Continuation-in-part of Ser. No. 861,777, Apr. 3, 1992, abandoned.

[51] Int. Cl.6 ............................................. A61B 5/04
[52] U.S. Cl. ................................. 128/710; 128/904
[58] Field of Search ................ 128/903, 904, 906, 710

[56] References Cited

U.S. PATENT DOCUMENTS

| | | | |
|---|---|---|---|
| 4,173,971 | 11/1979 | Karz | 128/904 |
| 4,216,462 | 8/1980 | McGrath et al. | 128/904 |
| 4,531,527 | 7/1985 | Reinhold, Jr. et al. | 128/904 |
| 4,974,607 | 12/1990 | Miwa | 128/904 |
| 5,020,540 | 6/1991 | Chamoun | 128/904 |
| 5,036,852 | 8/1991 | Leishman | 128/904 |
| 5,038,800 | 8/1991 | Oba | 128/904 |

OTHER PUBLICATIONS

"A system for remote computer electrocardiogram analysis via the switched telephone network" by T. P. de Jongh, in Medical and Biological Engineering & Computing, May 1977, p. 319.

Primary Examiner—William E. Kamm
Assistant Examiner—Scott M. Getzow

[57] ABSTRACT

The present invention, by using computer network technique to remotely treat EKG and EEH data, provides a useful way to make the EEMPI (EKG AND EEG MULTIPHASE INFORMATION DIAGNOSIS SYSTEM) to be used popularly in common people's home.

7 Claims, 3 Drawing Sheets

COMPUTER NETWORK EEMPI SYSTEM

This application is a continuation-in-part of U.S. Pat. No. application Ser. No. 07/861,777, filed Apr. 3, 1992, entitled Computer Network EEMPI System.

[Note: This is one of the improvements of the device EMPI Ser. No. 07/397,695 filed Oct. 30, 1989, and its CIP Ser. No. 07/822,525, filed Jan. 17, 1992, and also its CIP Ser. No. 07/994,492, filed Dec. 21, 1992, entitled Method of and Arrangement for Diagnosing Heart and Brain Desease.]

BACKGROUND OF THE INVENTION

The present invention relates to an improvement for EEMPI system, [EEMPI system, namely EKG and EEG Multiphase Information Diagnoser, (U.S. Patent Pending: Ser. No. 07/397,695 filed Oct. 30, 1989, and its CIP Ser. No. 07/822,525, filed Jan. 17, 1992, and also its CIP Ser. No. 07/994,492, filed Dec. 21, 1992, entitled Method of and Arrangement for Diagnosing Heart and Brain Disease.), is a device which could early detect, in a non-invasive manner, heart disease (especially coronary heart disease) before it can be detected by conventional methods], provides its remote usage and remote processing the data through computer network.

Dysfunction of the heart is still the leading cause of death in the world. About 48% of death in the U.S.A are caused by heart dysfunction. One of the major problems that had not been solved is the early detection of heart disease prior to the serious stages, such as a heart attack, at a time when the disease can be treated and progression might be rewarded or halted. Unfortunately, the conventional EKG can display normal results even in the presence of a patient's advanced coronary artery disease. The conventional EKG is neither sensitive nor specific enough to detect coronary artery disease which has led up to 50% of patients with occlusive coronary artery disease have been reported to have a normal conventional EKG.

Over the years many approaches have been utilized to extract information from the EKG regarding myocardial ischemia. Most of these techniques have been restricted to analysis in the time domain. More recently, in EKG field analysis involving quantification of the frequency content (such as power spectrum) or amplitude histogram of portions of EKG have been utilized. But all these transformations were used independently and have not been synthesized as an integral system. Plus some useful or new transformations, (i.e. transfer function, impulse response etc.), still have not been utilized in EKG field yet.

Since EKG signals arise from the discharge of hundreds of thousands of electrically active cells, they produce a complicated resultant complex electrical signal. This leads to challenging signal processing problems that conventional time and frequency domain analysis and isolated transformation analysis fail to address, since information regarding non-linearities, cross correlations, coherences, transmissions, phase relationships and the integral effect of all these factors combined are suppressed.

To solve this problem, a Multiphase Information Analysis techniques (MPI) is necessary. The definition of MPI is: an information analysis method which, by using a series of appropriate transformations (namely phases), transforms the original date (e.g. EKG) to a series of functions (namely MPI functions or MPI phases) such as power spectrum, transfer function, coherence, impulse response, cross correlation, and amplitude histogram, etc., then uses these MPI functions synthetically together and integrated as a system to extract the information which is difficult to be drawn with conventional methods. MPI is the main principle behind the EEMPI system. [Note: a series of functions are namely a series of phases, so this analysis method is called "Multiphase Information Analysis" (MPI) and the system for analyzing EKG (ELECTROCARDIOGRAM) and EEG (ELECTROENCEPHELOGRAM) is called EEMPI system (i.e. EKG AND EEG MULTIPHASE INFORMATION ANALYSIS SYSTEM)].

The definitions of the transformations used by EEMPI system are as follows:

The power spectrum function is calculated as follows: The auto power spectrum $G_{xx}(f)$ for lead V5, the signals of the chest lead of EKG(electrocardiogram), is determined from equation (1):

$$G_{xx}(f) = S_x(f) \cdot S_x(f)^* \quad (1)$$

where $S_x(f)$ is the Fourier transform of the time-dependent, lead V5 signal $f_x(t)$, and where $S_x(f)^*$ is the complex conjugate. For the power spectrum, the power is plotted against frequency.

The auto power spectrum $G_{yy}(f)$ for lead II is determined from equation (2):

$$G_{yy}(f) = S_y(f) \cdot S_y(f)^* \quad (2)$$

where $S_y(f)$ is the Fourier transform of the time-dependent, lead II signal, the signals of EKG limb lead, $f_y(t)$, and where $S_y(f)^*$ is the complex conjugate.

The phase shift function is calculated as follows: First, the amplitude ratio of the transfer function $H_{xy}(f)$ is determined from equation (3):

$$H_{xy}(f) = G_{xy}(f)/G_{xx}(f) \quad (3)$$

where the cross power spectrum:

$$G_{xy}(f) = S_x(f) \cdot S_y(f)^* \quad (4)$$

and where $G_{xx}(f)$ is obtained in equation (1).

Second, the phase shift $\theta_{xy}(f)$ of the transfer function $H_{xy}(f)$ is determined from equation (5):

$$\theta_{xy}(f) = \tan^{-1}\{[IM(H_{xy}(f))]/[RE(H_{xy}(f))]\}56 \quad (5)$$

where IM and RE are the imaginary and real parts of the transfer function.

The phase shift is a measure of the time difference between the left ventricular and whole heart signals and is plotted against frequency. Phase leads and lags are respectively indicated above and below the reference line, the base line.

The impulse response function is calculated as follows: The Impulse response $IH_x(f)$ is determined from equation (6):

$$IH_x(f) = F^{-1} H_{xy}(f) \quad (6)$$

where $F^{-1}$ is the inverse Fourier transform of the transfer function $H_{xy}(f)$ defined in equation (3).

The impulse response is a measure of the output response of the heart solely in response to the input of the left ventricular signal and is plotted as amplitude of impulse against the specific time T.

The amplitude histogram function is a standard statistical analysis of the amplitudes present in the left ventricular (EKG lead V5) and whole heart signals (EKG lead II), wherein the occurrence frequency is plotted against specific amplitudes. These plots indicate how many times a given amplitude is present in the left ventricular (EKG lead V5) and whole heat signals (EKG lead II).

The coherence function is calculated as follows: The coherence $\gamma_{xy}(f)$ is determined from equation (7):

$$\gamma_{xy}(f) = G_{xy}(f)/[G_{xx}(f) \cdot G_{yy}(f)] \tag{7}$$

$G_{xy}(f)$, $G_{xx}(f)$ and $G_{yy}(f)$ are defined in equations (4), (1) and (2). The coherence is plotted against frequency.

The cross correlation function is calculated as follows: The cross correlation $\phi_{xy}(\tau)$ is determined from equation (8):

$$\phi_{xy}(\tau) = \lim_{t \to \infty} 1/T \int f_x(t) \cdot f_y(t + \tau) dt \tag{8}$$

where $f_x(t)$ and $f_y(t)$ are the left ventricular (lead V5) and whole heart signals (lead II), whre $\tau$ is the delay time between the signals, and where T is the test period typically 150 seconds. The cross correlation is a measure of the correspondence of the signals and is plotted against the delay time $\tau$.

EEMPI system is a device which uses MPI technique to analyze EGK and EEG signals for early detecting, in a non-invasive manner, heart and brain disease before it can be detected by conventional methods. Unit now, no other device uses EMI techniques and 6 different kinds of transformations, as a system, to analyze EKG and EEG signals, therefore EEMPI is a totally new system (new invention), quite different from any other computerized EKG and conventional EKG and EEG system present today.

A specific but very important result of heart disease, especially coronary heart disease, is the heart attack and the onset of sudden death always happen unexpectedly, namely they may take place any time, and some times the attack happens in a non-symptomatic situation. This is called "silent ischemia". Therefore, it is prossible to find out the problems on time and deal with them prior to the serious stage only when the constant examination is available. This constant examination must be independent of doctors and of the hospitals, because it is difficult for every person to go to hospital and see a doctor at any time. On many occasions, it is too late for the patients to be hospitalized for the heart attack.

To achieve the goal of preventing sudden death from heart attacks and brain strokes, it is indispensable to develop an easily handled diagnostic instrument which can be used by patients themselves in the home to make an early diagnosis of heart disease especially coronary heart disease and an early warning of heart attack with constant monitoring independent of doctors or hospitals.

EEMPI is the only instrument that could be used to achieve this goal on the basis of its early diagnosis of heart disease, its easily handled by laymen, its automatically diagnosis, its light-weight and ability to be used in patient's home independent of doctors or hospitals. But it is still too expensive for the common people.

For solving this problem, one good way is to use a small piece of board to collect, amplify, A/D (analog to digit) convert the EKG data, and remotely transfer them to a diagnostic center through computer network (such as Moden System, Zoom 9600, etc.), then treat the data by the diagnostic center with EEMPI System and get the results (diagnosis of the patients), then transferring the results to the patients' (users, customers) computers to print out the results in their homes, that is the main principle of the present invention. By using of this invention, patients could use EMPI system in their homes only need to pay the cost of the collecter, amplifier, A/D converter and computer network, some software and accessories payments, that may be lower than $1,000.—which could be accepted (able burdening to pay) by most families.

It is therefore a principal object of the present invention by using computer network to remotely treat EKG and EEG data and make the EEMPI System, namely EKG and EEG Multiphase Information Diagnosis System, to be used popularly in common people's homes.

A further object of the present invention is to provide a way to remotely treat any biological and physical data (such as EMG, and many other biological and physical signals) with MPI system in a convenient condition.

SUMMARY OF THE INVENTION

The present invention, namely Computer Network EEMPI System, by using computer network technique to remotely treat EKG and EEG data, provides a useful way to make the EEMPI System to be used popularly in common people's homes. [EEMPI system, namely EKG and EEG Multiphase Information Diagnoser, (U.S. Patent Pending: Ser. No. 07/397.695 filed Oct. 30, 1989, and its CIP Ser. No. 07/822,525, filed Jan. 17, 1992), is a device which could early detect, in a non-invasive manner, heart disease (especially coronary heart disease) before it can be detected by conventional methods]. The present invention is a system comprises of seven main parts:

(1) The part for gathering, amplifying, A/D (analog to digit) converting, and saving the data. This part involves patient's cables set for gathering the EKG and EEG signals, amplifiers for amplifying the signals, A/D board for converting the analog signals of EKG and EEG to digital signals, filing the signals by the customers' (patients') computers, then saving them in a hardisk or floppydisk on the computers.

(2) Marking the signals and remote transferring them through computer network, such as Moden System, Zoom 9600, etc. This work is done by the customers' (patients') computers. Marking the signals means making a mark, a special code controlled by the diagnostic center, on the signals for denoting the signals are accepted to be treated by the center, and denoting the results shall be sent to the controlled customers.

(3) Receiving and checking the sources of signals. This work is done by the computers of the diagnostic centers, for checking the mark of the EKG and EEG signals transferred from the customers' computer to confirm whether the signals are accepted to be treated or not, and also check whether the signals are suitable to be treated, for instance, the signals with too much noise are unsuitable to be treated.

(4) Processing and treating the signals. This work is done by the EEMPI Systems in the diagnostic centers. Its results are the diagnosis of the patients.

(5) Marking the results and remote transferring them through computer network. The results from the diagnosis of the patients including its figures, should be marked according to the code controlled, then transferred to customers' computers according to the controlled code number.

(4) Receiving the results and checking the sources of signals. The results received by customers' computers should be checked. If its code is wrong, it should be denied, because it may be the diagnosis of another patient.

(7) Saving and printing out the results by the customers' computers, then the customers get their diagnosis from their own printers.

Parts (1) (2) (6) and (7) are used and performed by the customer's computer. Parts (3) (4) and (5) are performed by data processing center and its computers.

The present invention shall solve the problem of signal sources far beyond from the processing center. It is useful for remote processing of EKG and EEG signals gathering from the patients in their homes, and get the diagnosis from the diagnosis center in distance, to make the patient getting early diagnosis of heart and brain diseases conveniently, don't need them to go to hospitals frequently. Because the parts put in customers' computers are cheap, its cost may be less than $1,000. per unit, so this new invention shall cause the EEMPI System to be used popularity in common families.

Further features and advantages of the invention will be apparent from the description below.

BRIEF DESCRIPTION OF THE DRAWINGS

The invention is herein described, by way of example only, with reference in the accompanying drawings wherein.

DESCRIPTION OF A PREFERRED EMBODIMENT

I. The Key Point

The present invention relates to an improvement for the EEMPI system, [EEMPI system, namely EKG and EEG Multiphase Information Diagnoser, (U.S. Patent Pending: Ser. No. 07/397.695 filed Oct. 30, 1989, and its CIP Ser. No. 07/822,525, filed Jan. 17, 1992). It is a device which could early detect, in a non-invasive manner, heart disease (especially coronary heart disease) before it can be detected by conventional methods], provided by its remote usage and remote processing the data through a computer network.

The improvement comprises of seven main parts: (1) The first part is for gathering, amplifying, A/D (analog to digit) converting, and saving the signals; (2) Marking the signals and remote transferring them through computer network; (3) Receiving and checking the sources of signals; (4) Processing and treating the signals with EEMPI Systems; (5) Marking the results and remote transferring them through computer network; (6) Receiving and checking the sources of the results by the customers eempi computer; (7) Saving and printing out the results. Parts (1) (2) (6) and (7) are used and performed by the customer's computer. Parts (3) (4) and (5) are performed by data processing center and its computers. The present invention shall solve the problem of signal sources far beyond from the processing center. It is especially useful for remote processing of EKG and EEG signals gathered from the patients in their homes, and then receive the diagnosis from the diagnosis center far beyond the homes, to make early diagnosis of heart and brain diseases conveniently and eliminate the need of going to hospitals frequently. The parts in the customers' computers are cheap, its cost may be less than $1,000. per unit, so this new invention shall cause the EEMPI System to be used popularly in common families.

II. The Detailed Description

Figure 1:
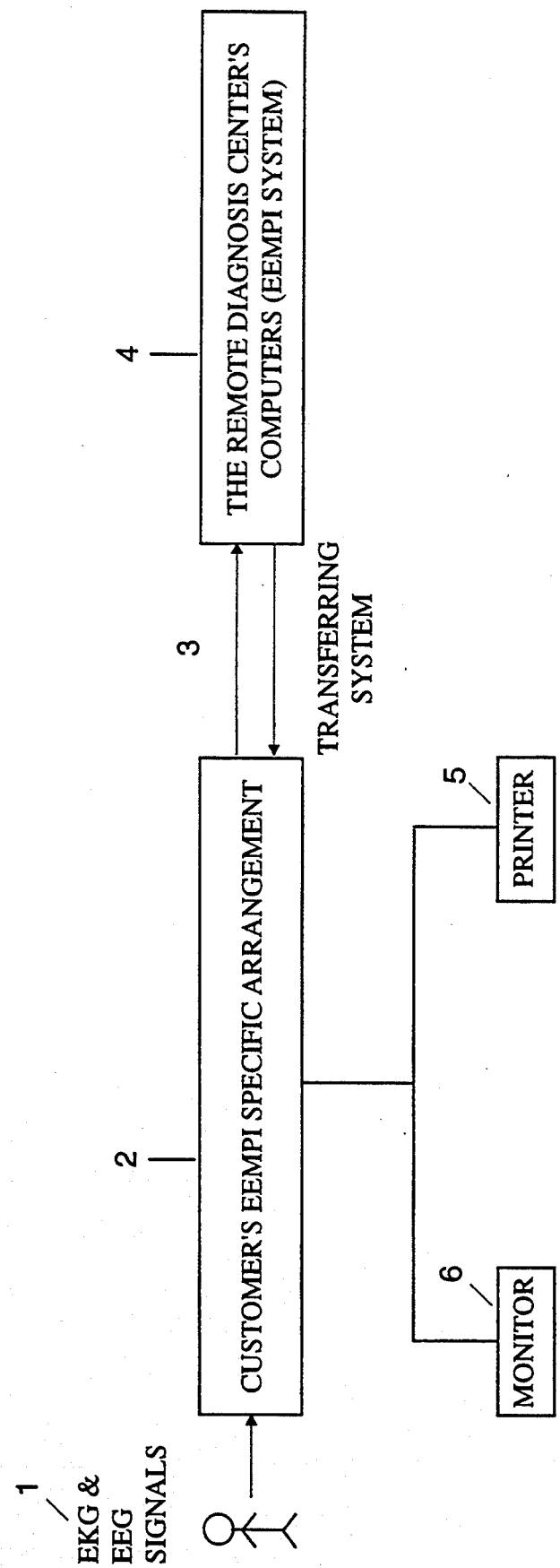
FIG. 1 is a diagram to illustrate the main constitute of the Computer Network EEMPI System and their main functions.

Referring to FIG. 1, it is a diagram illustrating the main constitute of one form of the Computer Network EEMPI System and their main functions. The EKG-/EEG signals 1 input to the customer's computer 2, after collecting, amplyfying, A/D (analog to digit) converting, saving and marking the signals, they are transferred to the computer of diagnostic center 4 through the computer network 3. The signals received by the computer of diagnostic center 4 are checked treated, and get the results (diagnosis), then the results are transferred to the customer's computer 2 through the computer network 3. The customer's computer 2 receives the results, checks them, then saves and prints out the results with a suitable printer 5 and displayed on the monitor 6.

Figure 2:
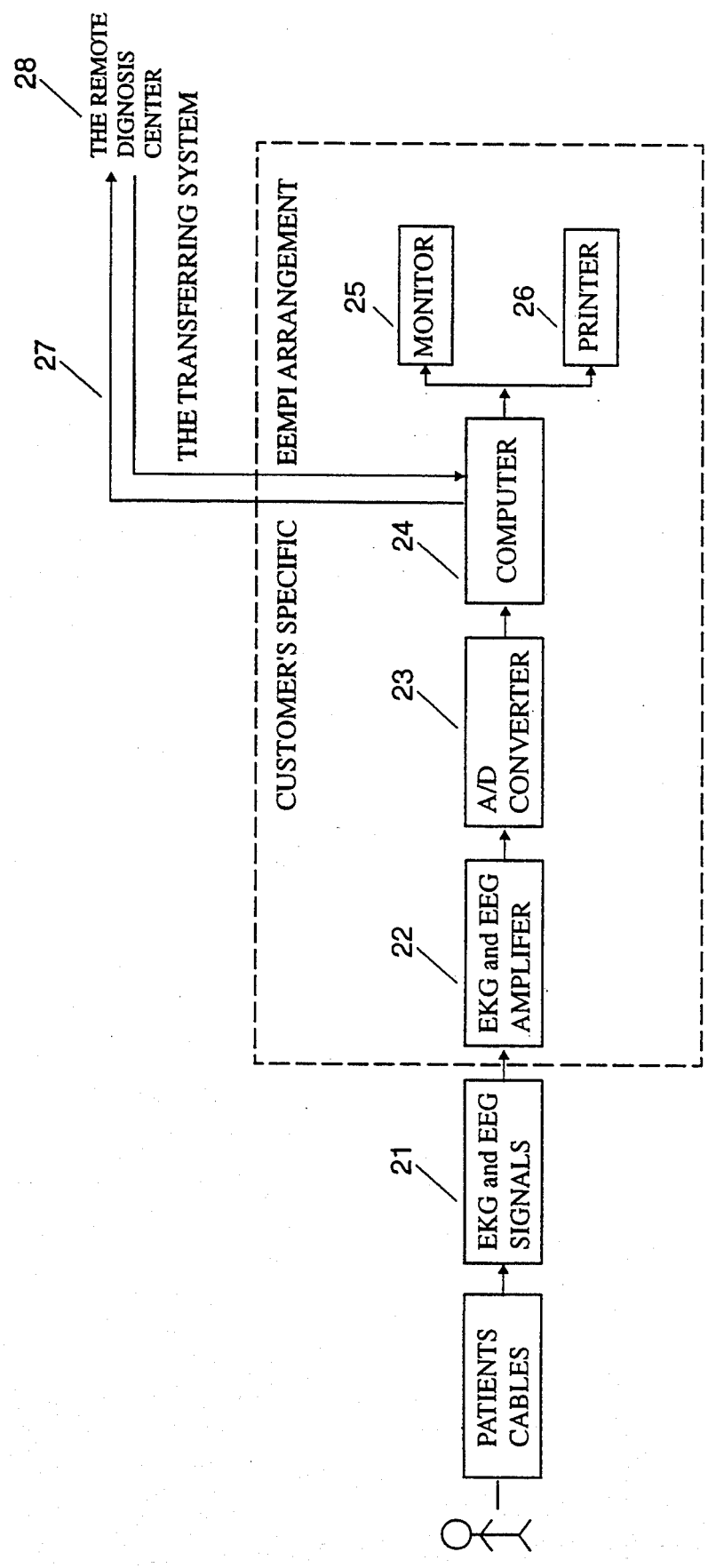
FIG. 2 is a diagram to show the main parts of the customer's computer.

FIG. 2 is a diagram to show the main parts of one form of the customer's computer. EKG/EEG signals through patients cable 21 inputed to the data collecter (amplifier) 22, the signals are amplified by the amplifier, then transferred to the A/D (analog to digit) converter 23 with which the analog signals of EKG/EEG are converted to digital signals. The digital signals are inputed to the customer's computer 24, the later 24 saves the marks the signals, then transfers them to the computer of diagnostic center 28 through the computer network 27. The signals received by the computer of the diagnostic center 28 are checked, then treated by EEMPI Systems and get the results (diagnosis of patients), then the results are transferred to the customer's computer 24 through the computer network 27. The customer's computer 2 receives the results, checks them, then saves and prints out the results with suitable printer 26 and shown on the monitor 25.

Figure 3:
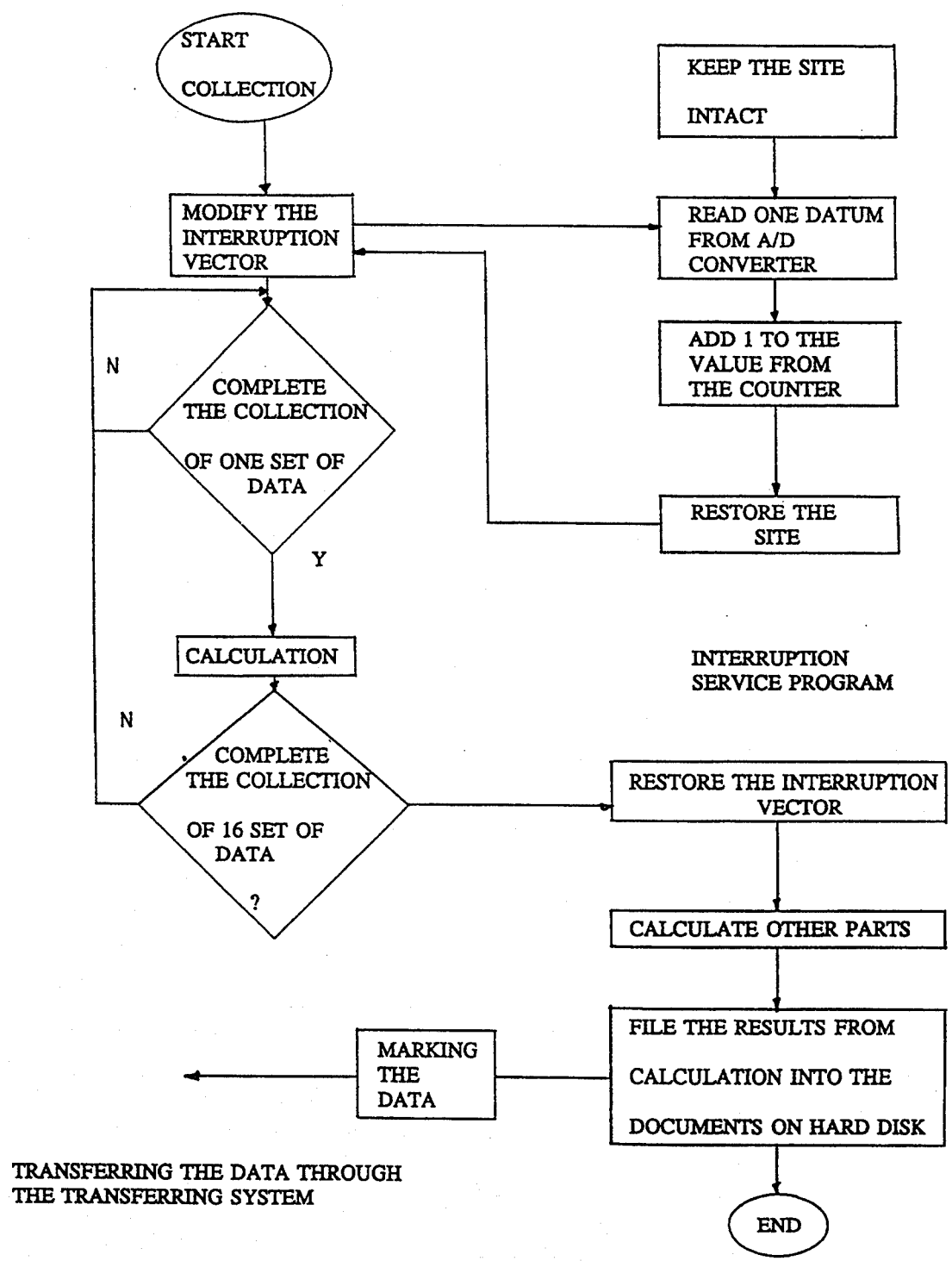
FIG. 3 is a flux chart of the software for collecting, saving and transferring the EKG and EEG data.

FIG. 3 is a flux chart of one form of the software for collecting, saving and transferring the EKG and EEG data.

It will be understood that each of the element described above, or two or more together, also may find a useful application in other types of constructions differing from the types described above.

While the invention has been illustrated and described as embodied in a method of and arrangement for diagnosing heart and brain disease, it is not intended to be limited to the details shown, since various modifications and structural changes may be made without departing in any way from the spirit of the present invention.

Without further analysis, the foregoing will fully reveal the gist of the present invention that others can, by applying current knowledge, readily adapt it for various applications without omitting features that, from the standpoint of prior art, fairly constitutes essential characteristics of the generic or specific aspects of this invention and, therefore, such adaptions should and are intended to be comprehended within the meaning and range of equivalence of the following claims.

What is claimed as new and desired to be protected by Letters Patent is set forth in the appended claims.

I claim:

1. A method for an EEMPI system, said method comprising the steps of:
   (1) An arrangement for detecting, amplifying, A/D (analog to digit) converting, and saving the EEMPI original signals provided by the EEMPI customer tested by the said arrangement;
   (2) Marking the said EEMPI original signals by the said arrangement and transferring them to a remote EEMPI diagnosis center through a remote transferring system;
   (3) Receiving and checking by the said EEMPI diagnosis center the said EEMPI original signals transferred from the said EEMPI customer;
   (4) Processing and treating the said EEMPI original signals with MPI (Multiphase Information Analysis) systems, and making EEMPI diagnosis for the said EEMPI customer by the said EEMPI diagnosis center;
   (5) Marking the said EEMPI diagnosis result of the said EEMPI customer and transferring the said result to the said customer through the said remote transferring system;
   (6) Receiving and checking (checking the marks said in (5)) of the said EEMPI diagnosis result by the said EEMPI customer's EEMPI arrangement (EEMPI specific arrangement);
   (7) Saving and printing out the said EEMPI diagnosis result by the said customer's arrangement (EEMPI specific arrangement);

2. The method according to claim 1, wherein the steps (1) (2) (6) and (7) are performed by the said EEMPI customer's EEMPI specific arrangement; steps (3) (4) and (5) are performed by the said EEMPI diagnosis center and its EEMPI systems.

3. The method according to claim 1, wherein the step (2) of marking the said EEMPI original signals and step (5) of marking the said EEMPI diagnosis result for the said EEMPI customer are performed according to a predetermined code which is matched with the said EEMPI customer's ID and the telephone number used by the said customer for transferring the said EEMPI original signals and the said EEMPI diagnosis result.

4. The method according to claim 1 step (1), wherein the said arrangement (EEMPI specific arrangement) is a computer which has a specific board for detecting, amplifying, A/D (analog to digit) converting, and saving the EEMPI original signals provided by the EEMPI customer tested by the said arrangement.

5. The method according to claim 1 (2), wherein the said remote tranferring system is a computer network.

6. The method according to claim 1 step (2), wherein the said remote transferring system is a telephone system.

7. The method according to claim 1 step (2), wherein the said remote transferring system is a Moden system.

* * * * *